US00PP15288P2

(12) United States Plant Patent
Olesen et al.

(10) Patent No.: US PP15,288 P2
(45) Date of Patent: Nov. 2, 2004

(54) FLORIBUNDA ROSE PLANT NAMED 'POULCS005'

(50) Latin Name: *Rosa hybrida*
Varietal Denomination: POULcs005

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 46 days.

(21) Appl. No.: 10/719,749

(22) Filed: Nov. 21, 2003

(51) Int. Cl.[7] ..... A01H 5/00
(52) U.S. Cl. ..... Plt./151
(58) Field of Search ..... Plt./151

*Primary Examiner*—Anne Marie Grunberg
*Assistant Examiner*—S B McCormick-Ewoldt

(57) ABSTRACT

A new garden rose plant of the floribunda class which has abundant red flowers and attractive foliage. This new and distinct variety has shown to be uniform and stable in the resulting generations from asexual propagation.

2 Drawing Sheets

Botanical classification: *Rose hybrida.*
Variety denomination: 'POULcs005'.

SUMMARY OF THE INVENTION

The present invention constitutes a new and distinct variety of garden rose plant which originated from a controlled crossing between an unnamed female parent and the male parent 'POULtry', described and illustrated in U.S. Plant patent application Ser. No. 10/155,860 dated May 24, 2002, now abandoned. The two parents were crossed during the summer of 1994 and the resulting seeds were planted in a controlled environment in Fredensborg, Denmark. The new variety is named 'POULcs005'.

The new variety may be distinguished from its unnamed seed parent, by the following combination of characteristics:

1. While the seed parent has dark pink flowers, 'POULcs005' has red flowers.
2. The seed parent has a wild rose scent, while 'POULcs005' has a moderate rose scent.
3. The seed parent has semi-double flowers and 'POULcs005' has very double flowers, 40–45 quantity.

The new variety may be distinguished from its pollen parent, 'POULtry' by the following combination of characteristics:

1. The pollen parent has Tudor formed flowers in dense tops; while 'POULcs005' is compact in even growth.
2. The pollen parent has a bud color as sepals unfold of Red-Purple Group 59A, while 'POULcs005' has a bud color as sepals unfold of Red-Purple Group 60B.
3. The pollen parent has little to no scent while 'POULcs005' has a moderate rose scent.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Disease resistance.

This combination of qualities is not present in previously available commercial cultivars of this type, known to the inventors, and distinguish 'POULcs005' from all other varieties of which we are aware.

As part of their rose development program, L. Pernille Olesen and Mogens N. Olesen germinated the seeds from the aforementioned hybridization during winter 1994 and conducted evaluations on the resulting seedlings in a controlled environment in Fredensborg, Denmark.

'POULcs005' was selected in the spring 1995 by the inventors as a single plant from the progeny of the aforementioned hybridization.

Asexual reproduction of 'POULcs005' by traditional budding and rooted cuttings was first done by L. Pernille and Mogens N. Olesen in their nursery in Fredensborg, Denmark in June, 1995. This initial and other subsequent asexual propagations conducted in controlled environments have demonstrated that the characteristics of 'POULcs005' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs005'. Specifically illustrated in SHEET 1:

FIG. 1.1; Open flower, stem showing open flower, branching, and the attachment of leaves, buds, and peduncles;

FIG. 1.2; Flower bud closed, flower bud as sepals unfold and flower bud partially open;

FIG. 1.3; Sepals, receptacle, and peduncle;

Specifically illustrated in SHEET 2;

FIG. 2.1; Flower petals detached;

FIG. 2.2; Bare stems exhibiting thorns;

FIG. 2.3; Juvenile leaf and mature leaf.

DETAILED DESCRIPTION OF THE VARIETY

The following is a description of 'POULcs005', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULcs001', a rose variety from the same inventors described and illustrated in U.S. Plant patent application Ser. No. 10/336,058 filed on Jan. 3, 2003 are compared to 'POULcs005' in Chart 1.

CHART 1

| | 'POULcs005' | 'POULcs001' |
|---|---|---|
| Bud color | Red Purple Group 60B. | Red Group 46A. |
| Petal count | 40 to 45. | 24 to 26. |
| Thorn | Greyed-Purple Group 183A. | Greyed-Yellow Group 160C. |

Parents:

*Seed parent.*—Unnamed seedling.

*Pollen parent.*—'POULtry'.

FLOWER AND FLOWER BUD

Blooming habit: Continuous.

Flower bud:

*Size.*—Upon opening, 32 mm in length from base of receptacle to end of bud.

*Bud form.*—Pointed ovoid.

*Bud color.*—As sepals unfold, petals are Red-Purple Group 60B. At ¼ opening petals are Red-Purple Group 60B.

*Sepals.*—Upper Surface: Color: Yellow-Green Group 145B. Shape: Surfaces of sepals are moderately pubescent. Lower Surface: Color: Yellow-Green Group 144B with intonations of anthocyanin the color of Greyed-Purple 183D. Texture: Smooth with many stipitate glands. Shape: Sepal apex is cirrhose. Base is flat at union with receptacle. Margins have medium foliaceous appendages on three of the five sepals. Surfaces of sepals are moderately pubescent. Size: 28 mm to 35 mm (l) by 7 mm to 9 mm (w).

*Receptacle.*—Surface Texture: Glaucous. Shape: Urn-shaped. Size: 7 mm (h)×6 mm (w). Color: Yellow-Green Group 145B. Anthocyanin: None observed.

*Peduncle.*—Surface: Stipitate glands observed in generous quantity. Length: 50 mm to 80 mm average length. Color: Greyed Purple Group 185A. Strength: Somewhat strong.

*Borne.*—Multiple buds per stem. On average 4 buds per stem.

*Anthocyanin.*—None observed.

Flower bloom:

*Fragrance.*—Moderate rose scent.

*Duration.*—The blooms have a duration on the plant of approximately 7 to 10 days. Petals fall cleanly away from plant.

*Size.*—Average flower diameter is 75 mm when open.

*Form.*—General shape is an open cup, double flower, with petals that are reflexed. Shape of flower when viewed from the side: Upon opening, upper part: Flattened convex. Upon opening, lower part: Flattened convex. Open flower, upper part: Flattened convex. Open flower, lower part: Concave.

*Petalage.*—Very double. Average range: 40 to 45 petals under normal conditions with 11 petaloids.

Color:

*Upon opening, petals.*—Outermost petals: Outer side: Red-Purple Group 60B. Inner Side: Red-Purple Group 60A. Innermost petals: Outer side: Red-Purple Group 60B. Inner Side: Red-Purple Group 60A.

*Upon opening, basal petal spots.*—Outermost petals: Outer side: White Group 155B with a weak intonation of Yellow Group 4B. Inner Side: White Group 155B with a weak intonation of Yellow Group 4B. Innermost petals: Outer side: White Group 155B with a weak intonation of Yellow Group 4B. Inner Side: White Group 155B with a weak intonation of Yellow Group 4B.

*After opening, petals.*—Outermost petals: Outer side: Red-Purple Group 61B. Inner Side: Red-Purple Group 60A. Innermost petals: Outer side: Red-Purple Group 61B to 61C. Inner Side: Red-Purple Group 60B to 61B.

*After opening, basal petal spots.*—Outermost petals: Outer side: White Group 155B with a weak intonation of Yellow Group 4B. Inner Side: White Group 155B with a weak intonation of Yellow Group 4B. Innermost petals: Outer side: White Group 155B with a weak intonation of Yellow Group 4B. Inner Side: White Group 155B with a weak intonation of Yellow Group 4B.

General tonality: On open flower Red-Purple Group 60B to 61B. No change in the general tonality at the end of the 10th day. Afterwards, general tonality is Red-Purple Group 60B to 61B.

Petals:

*Petal reflex.*—Weak reflex of petal margin.

*Margin.*—Entire and uniform. Typically reflexed along margin with weak undulation of margin.

*Shape.*—Apex: Round. Base: Acute.

*Size.*—35 mm to 45 mm (l)×35 mm to 45 mm (w).

*Texture.*—Smooth.

*Thickness.*—Thick to Average.

*Arrangement.*—Not Formal.

Petaloids:

*Quantity.*—10 to 12.

*Color.*—Red-Purple Group 60B to 57A.

*Size.*—28 mm (l)×26 mm (w).

Reproductive organs:

*Pistils.*—Length: 5 mm long. Quantity: 55.

*Pollen.*—Color: Yellow-Orange Group 23A. Quantity: Scant.

*Anthers.*—Size: 2 mm to 3 mm long. Color: Yellow-Orange Group 23A. Quantity: 42 actual count.

*Filaments.*—Color: Yellow Group 13A. Length: 3 mm to 4 mm.

*Stigmas.*—Superior in location to anthers. Color: Greyed-Yellow Group 160C.

*Styles.*—Color: Greyed-Yellow Group 160C.

*Hips.*—None observed in the field nursery in Jackson County Oreg.

PLANT

Plant growth: Vigorous, upright to bushy.

Stems:

*Color.*—Young wood: Yellow-Green Group 144B with strong intonations of Greyed-Purple Group 183B. Older wood: Yellow-Green Group 144B with strong intonations of Greyed-Purple Group 183B.

*Surface texture*.—Young wood: Smooth. Older wood: Smooth. Anthocyanin: Greyed-Purple Group 183B.

*Thorns*.—Incidence: 9 thorns per 10 cm of stem. Size: Average length: 6 mm. Color: Greyed-Purple Group 183A. Shape: Deeply concave to concave.

Plant foliage: Normal number of leaflets on normal leaves in middle of the stem: 7 leaflets.

*Compound leaf size*.—32 mm to 40 mm (l)×25 mm to 34 mm (w).

*Color*.—Mature Foliage: Upper Leaf Surface: Yellow-Green Group 146A to 147B. Lower Leaf Surface: Yellow-Green Group 146C. Juvenile foliage: Upper Leaf Surface: Yellow-Green Group 144B. Lower Leaf Surface: Yellow-Green Group 144B. Anthocyanin: Location: Weak intonation of Greyed-Yellow Group 181B at leaf margins on juvenile leaves.

Plant leaves and leaflets:

*Stipules*.—Size: 20 mm. Color: Yellow-Green Group 144C. Margins: Finely serrated with many stipitate glands. Anthocyanin: None observed.

*Petiole*.—Length: 30 mm to 45 mm. Color: Yellow-Green Group 145B. Margins: Stipitate glands present. Anthocyanin: Greyed-Red Group 182A.

*Rachis*.—Length: 30 mm to 45 mm. Color: Yellow-Green Group 145B. Margins: Stipitate glands present. Anthocyanin: Greyed-Red Group 182A.

*Leaflet*.—Edge: Serrated. Shape: Ovate to round. Apex: Round. Base: Acute. Texture: Average thickness. Arrangement: Odd pinnate. Venation: Reticulate. Glossiness: Moderately Glossy.

Disease resistance: Above average resistance to mildew, rust, black spot, and Botrytis under normal growing conditions in Jackson County, Oreg.

Cold hardiness: The variety 'POULcs005' has been found to be cold tolerant to USDA Cold Hardiness Zone 6.

It is claimed:

1. A new and distinct variety of rose plant of the floribunda rose class, substantially as herein illustrated and described as a distinct and novel rose variety due to its abundant red flowers, disease resistance, and extended period of bloom.

* * * * *

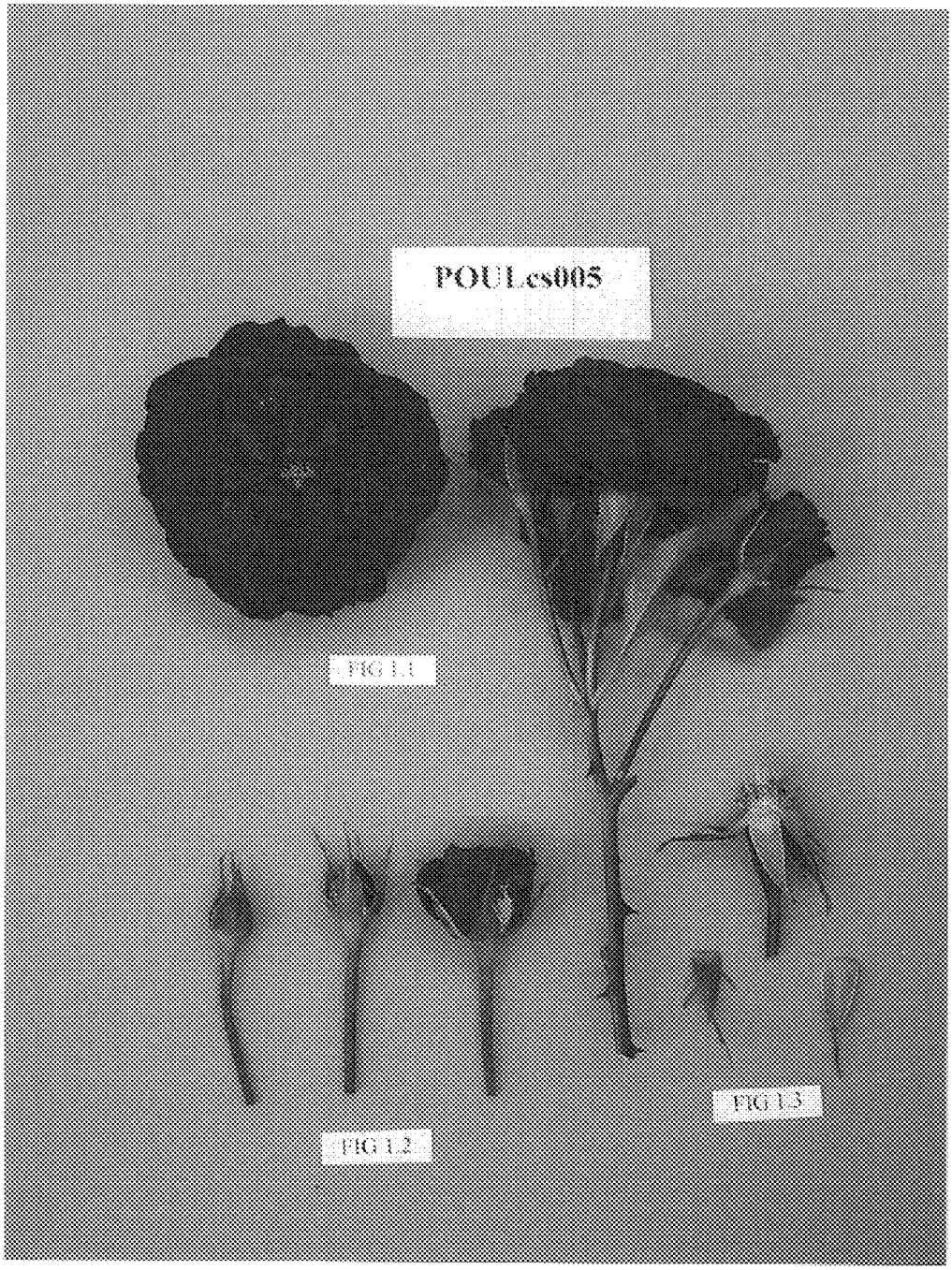
POULcs005
FIG 1.1
FIG 1.2
FIG 1.3

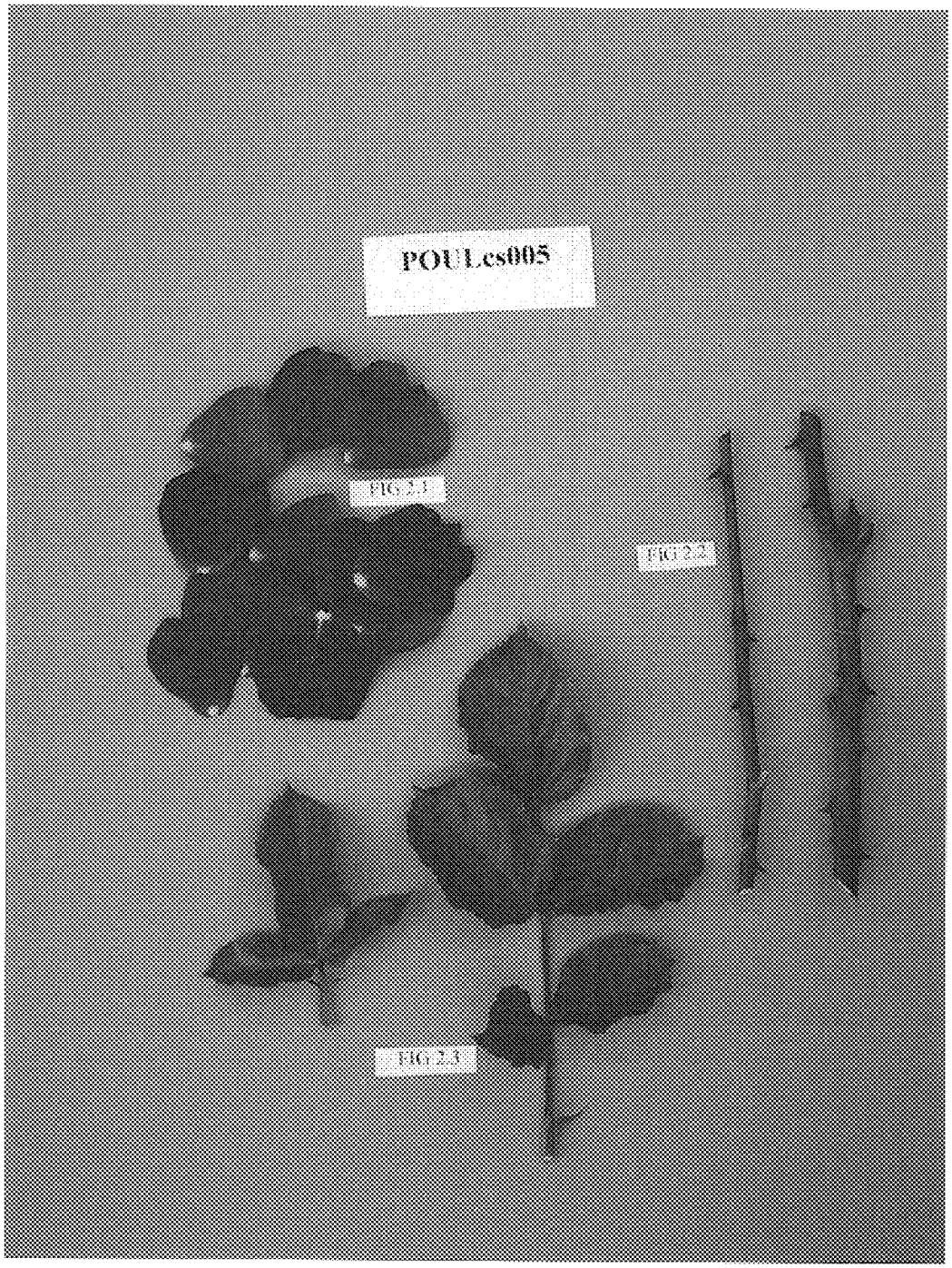
POULes005
FIG 2.1
FIG 2.2
FIG 2.3